(12) United States Patent
Shur et al.

(10) Patent No.: US 8,384,047 B2
(45) Date of Patent: Feb. 26, 2013

(54) FLUORESCENCE-BASED ULTRAVIOLET ILLUMINATION

(75) Inventors: Michael Shur, Latham, NY (US); Steven J. Britz, Laurel, MD (US)

(73) Assignees: Sensor Electronic Technology, Inc., Columbia, SC (US); The United States of America, as Represented by the Secretary of Agriculture, Washington, DC (US)

( * ) Notice: Subject to any disclaimer, the term of this patent is extended or adjusted under 35 U.S.C. 154(b) by 100 days.

(21) Appl. No.: 12/973,988

(22) Filed: Dec. 21, 2010

(65) Prior Publication Data

US 2011/0147617 A1 Jun. 23, 2011

Related U.S. Application Data

(60) Provisional application No. 61/288,679, filed on Dec. 21, 2009.

(51) Int. Cl.
*G01N 21/64* (2006.01)
(52) U.S. Cl. .............. 250/461.1; 250/458.1; 250/459.1
(58) Field of Classification Search .............. 250/461.1
See application file for complete search history.

(56) References Cited

U.S. PATENT DOCUMENTS

| | | | |
|---|---|---|---|
| 4,506,474 A | 3/1985 | Kadkade et al. | |
| 5,014,225 A * | 5/1991 | Vidaver et al. | 702/19 |
| 5,040,329 A | 8/1991 | Michaloski | |
| 7,112,806 B2 * | 9/2006 | Lussier | 250/458.1 |
| 7,553,456 B2 | 6/2009 | Gaska et al. | |
| 7,634,996 B2 | 12/2009 | Gaska et al. | |
| 2007/0196235 A1 | 8/2007 | Shur et al. | |
| 2009/0280035 A1 | 11/2009 | Koudymov et al. | |
| 2010/0181496 A1 * | 7/2010 | Moise et al. | 250/459.1 |
| 2010/0296971 A1 | 11/2010 | Gaska et al. | |
| 2011/0297848 A1 * | 12/2011 | Haidekker et al. | 250/459.1 |

* cited by examiner

*Primary Examiner* — Marcus Taningco
(74) *Attorney, Agent, or Firm* — John W. LaBatt; Hoffman Warnick LLC (57) ABSTRACT

A solution for managing illumination of an organism with ultraviolet light is provided. A set of ultraviolet fluorescence characteristics of the organism can be determined using fluorescence data for the organism. The set of ultraviolet fluorescence characteristics can be used to determine a set of target properties of the ultraviolet light. The set of target properties can be used to illuminate the organism with ultraviolet light. The illumination can be managed during growth of the organism, breeding of the organism, and/or maintenance of the organism after harvest.

20 Claims, 4 Drawing Sheets

FLUORESCENCE-BASED ULTRAVIOLET ILLUMINATION

REFERENCE TO PRIOR APPLICATIONS

The current application claims the benefit of co-pending U.S. Provisional Application No. 61/288,679, titled "Ultraviolet Illumination System for Plant Growth, Storage, and Breeding", which was filed on 21 Dec. 2009, and which is hereby incorporated by reference.

TECHNICAL FIELD

The disclosure relates generally to ultraviolet illumination of an organism, and more particularly, to determining a target property of the ultraviolet illumination using fluorescence characteristics of the organism.

BACKGROUND ART

Ultraviolet radiation has been used for sterilization and killing microorganisms. For example, ultraviolet energy in the germicidal band for grape vines on a vineyard trellis has been used to provide a lethal exposure (irradiation) for the purpose of eradicating microorganisms, and stimulating host plant defense mechanisms. It is also known that crop yields can be enhanced by visible light exposure during night.

Recently, interest has increased in protected cultivation (e.g., greenhouses) to grow high quality local vegetables, especially early and late in the season. However, many coverings commonly used for greenhouses also block ultraviolet (UV) light. Most plants respond to UV light by initiating or increasing the synthesis of polyphenolic compounds, such as flavonoids, which absorb incident UV light and protect plant tissues from DNA damage that might otherwise result from UV light exposure. These compounds also are potent antioxidants and can affect cell metabolism (e.g., nitric oxide levels). Thus, the compounds may be important components of mammalian diets. Consequently, growing plants in protected cultivation may reduce their nutritional value.

A current approach to manipulate the UV environment in greenhouses utilizes coverings that allow UV light to pass through. However, such coverings have little benefit early and late in a growing season when ambient UV radiation is reduced because the sun is lower in the sky. Fluorescent sun lamps have been used to enhance polyphenolics in plants, but they are inefficient and, in addition, are breakable and contain mercury. Currently available deep UV light emitting diodes (DUV-LEDs) offer the possibility of a higher efficiency and safer UV light for protected cultivation, but these sources are still early in development and very dim.

SUMMARY OF THE INVENTION

Nonetheless, the inventors surprisingly found that forty-eight hour exposure to UV light emitted by DUV-LEDs (282 nanometer peak wavelength) resulted in greater than two-fold increases in two different flavonoids, Cyanidin and Quercetin, in red leaf lettuce grown in simulated winter greenhouse conditions. Cyanidin is a red pigment found in many fruits and vegetables. Thus, treatment with a wavelength that is essentially absent in sunlight dramatically enhanced both the concentration of nutritionally-important phytochemicals and the visual appearance of a widely-grown greenhouse crop. Similar effects may be possible in plants treated with UV light in the cold after harvest. Although the quantitative requirements for UV light in different species and genetic lines is not fully understood, DUV-LEDs are likely to find wide spread application in crop growth and storage. To this extent, solid-state UV devices could be implemented in other aspects of horticultural lighting, such as photosynthetic supplementation, control of flowering, and/or the like. Aspects of the invention provide an approach to develop and utilize an effective ultraviolet light illumination cycle (e.g., protocol), which can be implemented using solid-state UV devices.

Aspects of the invention provide a solution for managing illumination of an organism with ultraviolet light. A set of ultraviolet fluorescence characteristics of the organism can be determined using fluorescence data for the organism. The set of ultraviolet fluorescence characteristics can be used to determine a set of target properties of the ultraviolet light. The set of target properties can be used to illuminate the organism with ultraviolet light.

A first aspect of the invention provides a method comprising: managing at least one condition of an environment of an organism for a managed time period using a computer system, the managing including repeatedly, during the managed time period: determining a set of ultraviolet fluorescence characteristics of the organism using ultraviolet fluorescence data for the organism, wherein the ultraviolet fluorescence data is acquired while the organism is illuminated with ultraviolet light; determining a set of target properties of the ultraviolet light based on the set of ultraviolet fluorescence characteristics; and providing the set of target properties for use in illuminating the organism with ultraviolet light.

A second aspect of the invention provides a system comprising: a computer system including at least one computing device for managing at least one condition of an environment of an organism for a managed time period, the managing including repeatedly, during the managed time period: determining a set of ultraviolet fluorescence characteristics of the organism using ultraviolet fluorescence data for the organism, wherein the ultraviolet fluorescence data is acquired while the organism is illuminated with ultraviolet light; determining a set of target properties of the ultraviolet light based on the set of ultraviolet fluorescence characteristics; and providing the set of target properties for use in illuminating the organism with ultraviolet light.

A third aspect of the invention provides a computer program comprising program code embodied in at least one computer-readable medium, which when executed, enables a computer system to implement a method of managing at least one condition of an environment of an organism for a managed time period, the method comprising: determining a set of ultraviolet fluorescence characteristics of the organism using ultraviolet fluorescence data for the organism, wherein the ultraviolet fluorescence data is acquired while the organism is illuminated with ultraviolet light; determining a set of target properties of the ultraviolet light based on the set of ultraviolet fluorescence characteristics; and providing the set of target properties for use in illuminating the organism with ultraviolet light.

Other aspects of the invention provide methods, systems, program products, and methods of using and generating each, which include and/or implement some or all of the actions described herein. The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, aspects of the invention provide a solution for managing illumination of an organism with ultraviolet light. A set of ultraviolet fluorescence characteristics of the organism can be determined using fluorescence data for the organism. The set of ultraviolet fluorescence characteristics can be used to determine a set of target properties of the ultraviolet light. The set of target properties can be used to illuminate the organism with ultraviolet light. The illumination can be managed during growth of the organism, breeding of the organism, and/or maintenance of the organism after harvest. The illumination can increase crop yields, increase/maintain a quality of the crop, reduce fouling of water borne vehicles, and/or the like. As used herein, unless otherwise noted, the term "set" means one or more (i.e., at least one) and the phrase "any solution" means any now known or later developed solution.

Figure 1:
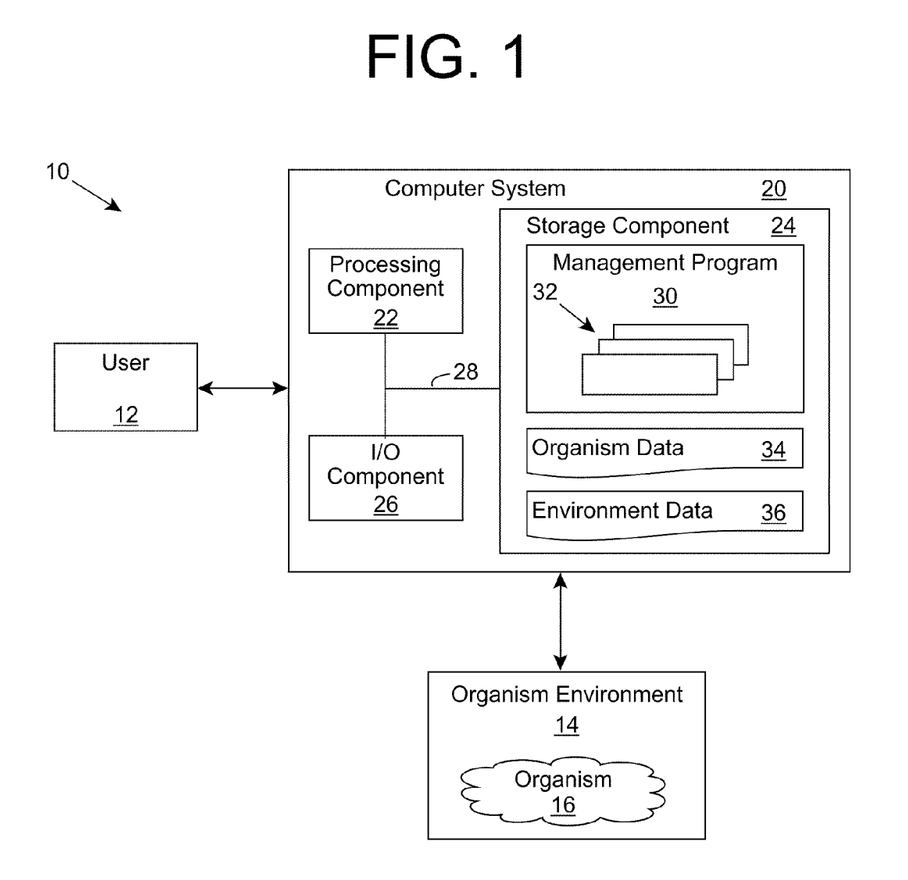
FIG. 1 shows an illustrative computing environment for managing one or more conditions of an environment of an organism according to an embodiment.

Turning to the drawings, FIG. 1 shows an illustrative computing environment 10 for managing one or more conditions of an organism environment 14 of an organism 16 according to an embodiment. To this extent, computing environment 10 includes a computer system 20 that can perform a process described herein in order to manage one or more conditions of the organism environment 14 of the organism 16. In particular, computer system 20 is shown including a management program 30, which makes computer system 20 operable to manage one or more conditions of the organism environment 14 of the organism 16 by performing a process described herein.

Computer system 20 is shown including a processing component 22 (e.g., one or more processors), a storage component 24 (e.g., a storage hierarchy), an input/output (I/O) component 26 (e.g., one or more I/O interfaces and/or devices), and a communications pathway 28. In general, processing component 22 executes program code, such as management program 30, which is at least partially fixed in storage component 24. While executing program code, processing component 22 can process data, which can result in reading and/or writing transformed data from/to storage component 24 and/or I/O component 26 for further processing. Pathway 28 provides a communications link between each of the components in computer system 20. I/O component 26 can comprise one or more human I/O devices, which enable a human user 12 to interact with computer system 20 and/or one or more communications devices to enable a system user 12 to communicate with computer system 20 using any type of communications link. To this extent, management program 30 can manage a set of interfaces (e.g., graphical user interface(s), application program interface, and/or the like) that enable human and/or system users 12 to interact with management program 30. I/O component 26 also can comprise one or more sensing and/or emitting devices, which enable computer system 20 to acquire data on and/or alter one or more conditions of the organism environment 14 and/or the organism 16. Further, management program 30 can manage (e.g., store, retrieve, create, manipulate, organize, present, etc.) the data, such as organism data 34 and/or environment data 36, using any solution.

In any event, computer system 20 can comprise one or more general purpose computing articles of manufacture (e.g., computing devices) capable of executing program code, such as management program 30, installed thereon. As used herein, it is understood that "program code" means any collection of instructions, in any language, code or notation, that cause a computing device having an information processing capability to perform a particular action either directly or after any combination of the following: (a) conversion to another language, code or notation; (b) reproduction in a different material form; and/or (c) decompression. To this extent, management program 30 can be embodied as any combination of system software and/or application software.

Further, management program 30 can be implemented using a set of modules 32. In this case, a module 32 can enable computer system 20 to perform a set of tasks used by management program 30, and can be separately developed and/or implemented apart from other portions of management program 30. As used herein, the term "component" means any configuration of hardware, with or without software, which implements the functionality described in conjunction therewith using any solution, while the term "module" means program code that enables a computer system 20 to implement the actions described in conjunction therewith using any solution. When fixed in a storage component 24 of a computer system 20 that includes a processing component 22, a module is a substantial portion of a component that implements the actions. Regardless, it is understood that two or more components, modules, and/or systems may share some/all of their respective hardware and/or software. Further, it is understood that some of the functionality discussed herein may not be implemented or additional functionality may be included as part of computer system 20.

When computer system 20 comprises multiple computing devices, each computing device can have only a portion of management program 30 fixed thereon (e.g., one or more modules 32). However, it is understood that computer system 20 and management program 30 are only representative of various possible equivalent computer systems that may perform a process described herein. To this extent, in other embodiments, the functionality provided by computer system 20 and management program 30 can be at least partially implemented by one or more computing devices that include any combination of general and/or specific purpose hardware with or without program code. In each embodiment, the hardware and program code, if included, can be created using standard engineering and programming techniques, respectively.

Regardless, when computer system 20 includes multiple computing devices, the computing devices can communicate over any type of communications link. Further, while performing a process described herein, computer system 20 can communicate with one or more other computer systems using any type of communications link. In either case, the communications link can comprise any combination of various types of wired and/or wireless links; comprise any combination of one or more types of networks; and/or utilize any combination of various types of transmission techniques and protocols.

As discussed herein, management program 30 enables computer system 20 to manage the organism environment 14 of the organism 16. The organism 16 can comprise any type of organism, including a plant, animal, fungus, and/or the like. The organism environment 14 can comprise a natural and/or artificial environment in which the organism 16 is growing, reproducing, is maintained (e.g., stored, transported, and/or the like) after harvesting, and/or the like. To this extent, computer system 20 can manage one or more conditions of the organism environment 14 to make the environment favorable for the growth, reproduction, maintenance (e.g., preservation and/or conservation), and/or the like, of the organism 16.

While managing the condition(s) of the organism environment 14, computer system 20 can obtain, process, and/or generate organism data 34 and environment data 36 using any solution. To this extent, computer system 20 can acquire organism data 34, which corresponds to one or more attributes of the organism 16 using any solution. Illustrative attributes of the organism 16 include various physical attributes of the organism, such as its size, color, weight, fluorescence, and/or the like. Similarly, computer system 20 can acquire environment data 36, which corresponds to one or more conditions of the organism environment 14 using any solution. Illustrative conditions of the organism environment 14 include temperature, humidity, one or more aspects of soil and/or water content (e.g., level of one or more nutrients), one or more properties of visible/non-visible lighting (e.g., spectral content, intensity, and/or the like), and/or the like. In an embodiment, computer system 20 (e.g., I/O component 26) includes a set of sensors, each of which is configured to acquire data regarding a set of attributes of the organism 16 and/or a set of conditions of the organism environment 14. The sensors can be fixed in the organism environment 14 or temporarily positioned to acquire the data. Computer system 20 can operate, interrogate, and/or acquire data directly from the sensors using any solution. Additionally, computer system 20 can obtain some or all of the organism data 34 and/or environment data 36 from another computer system, which manages sensors apart from computer system 20.

In addition to sensor data, organism data 34 and/or environment data 36 can comprise a set of rules, which define one or more target attributes of the organism 16 and/or target conditions of the organism environment 14. For example, organism data 34 can include a set of rules, which define a target color, fluorescence, and/or the like, for the organism 16. Furthermore, environment data 36 can comprise a set of rules, which define a target temperature, humidity level, nutrient level, lighting level, and/or the like, for the organism environment 14. Similarly, the set of rules for organism data 34 and/or environment data 36 can define a time at which one or more target attributes of the organism 16 and/or target conditions of the organism environment 14 changes, a set of actions for obtaining a target attribute of the organism 16 and/or a target condition of the organism environment 14 when the actual attribute/condition differs from the target attribute/condition, and/or the like.

Computer system 20 can process organism data 34 and/or environment data 36 and perform one or more actions in response to the organism data 34 and/or environment data 36. For example, computer system 20 (e.g., I/O component 26) can comprise one or more climate control devices, such as emission and/or dispensing devices, heating/cooling devices, humidity control devices, and/or the like, which computer system 20 can operate to adjust one or more conditions of the organism environment 14 based on the organism data 34 and/or environment data 36. Additionally, computer system 20 can provide data corresponding to the one or more actions for processing by another computer system, which manages the operation of one or more climate control devices apart from computer system 20.

In an embodiment, computer system 20 manages illumination of the organism 16 with ultraviolet light during a managed time period. To this extent, computer system 20 can determine one or more target properties of the ultraviolet light based on one or more characteristics of the organism 16. For example, computer system 20 can determine a set of target properties of the ultraviolet light comprising one or more of: a target spectrum, a target intensity, a target polarization, a target spatial pattern of radiation, and/or the like. Additionally, computer system 20 can determine one or more aspects of illuminating the organism 16, such as a start time, a duration, constant versus pulsed, and/or the like.

Figure 2:
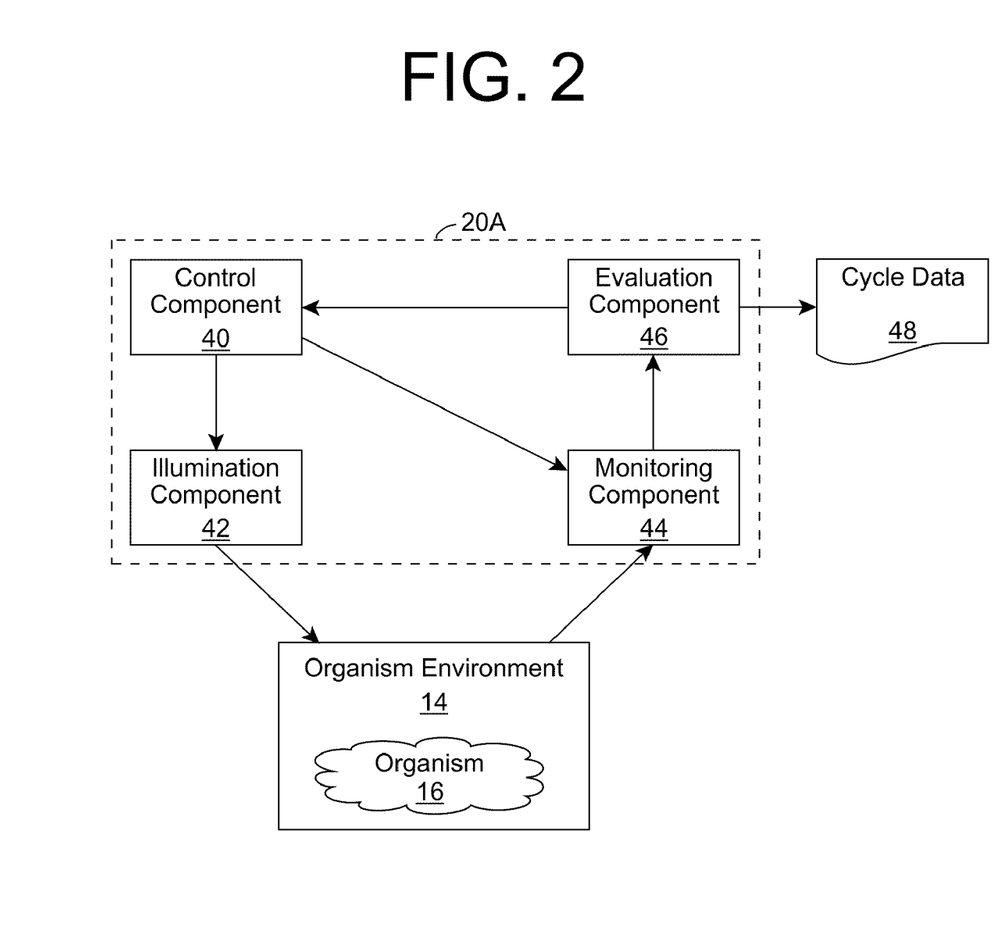
FIG. 2 shows a component view of another illustrative computer system according to an embodiment.

Computer system 20 can dynamically determine the set of target properties of the ultraviolet light while managing illumination of the organism 16 during the managed period. To this extent, FIG. 2 shows a component view of another illustrative computer system 20A according to an embodiment. Computer system 20A includes a control component 40, which can operate one or more devices in an illumination component 42 to illuminate the organism 16 within the organism environment 14 with ultraviolet and/or visible light. Additionally, control component 40 can operate one or more devices in a monitoring component 44 to acquire data regarding the organism environment 14 and/or the organism 16. The data can be provided to an evaluation component 46, which can evaluate the data regarding the organism environment 14 and/or the organism 16, and provide a result of the evaluation to the control component 40, which can adjust one or more aspects of the operation of illumination component 42 and/or monitoring component 44 based on the evaluation.

Illumination component 42 includes a set of light emitting devices, which are configured to illuminate the organism 16 within the organism environment 14. The light generated by illumination component 42 can be used to supplement and/or replace natural light (e.g., daylight) within the organism environment 14. To this extent, some or all of the set of light emitting devices can be mounted within the organism environment 14 such that light emitted by the device(s) is directed onto the organism 16. Additionally, the organism environment 14 can include a wave guiding structure or the like, which directs light emitted by one or more externally or internally located light emitting devices to a desired location within the organism environment 14.

Illumination component 42 can include any combination of various types of light emitting devices. For example, illumination component 42 can include one or more visible light emitting devices, such as any of various types of electrically powered visible light sources. The visible light emitting devices can generate light having a broad spectrum (e.g., white light) and/or generate chromatic (e.g., non-white) light. Still further, illumination component 42 can generate chromatic light from a white light emitting device using one or more filters and/or the like. In an embodiment, illumination component includes devices for illuminating the organism 16 with chromatic visible light, such as blue light, red light, and/or the like. Additionally, illumination component 42 can include a set of ultraviolet (UV) light emitting devices. In an embodiment, illumination component 42 includes a set of deep ultraviolet (DUV) light emitting devices, which emit ultraviolet light having a peak wavelength between approximately 200 nanometers (nm) and approximately 340 nm.

In another illustrative embodiment, illumination component 42 includes one or more light emitting devices implemented using a set of light emitting diodes (LEDs). The set of LEDs can include one or more LEDs configured to generate light emitted over a broad spectrum (e.g., white light), one or more LEDs configured to generate chromatic light (e.g., blue, red, and/or the like), and/or one or more DUV LEDs. While various aspects of the invention are described further with reference to LEDs, it is understood that any combination of various types of visible, UV, and/or DUV light sources can be utilized (e.g., semiconductor laser, laser, mercury lamp, halogen lamp, and/or the like). When illumination component 42 includes one or more UV/DUV light emitting devices, illumination component 42 can include visual and/or audible alert devices, which can signal a human user 12 (FIG. 1) when the UV/DUV light emitting devices are on/going to be turned on.

Monitoring component 44 can include any combination of various types of sensing devices for acquiring organism data 34 (FIG. 1) corresponding to the organism 16 and/or environment data 36 (FIG. 1) corresponding to the organism environment 14. Control component 40 can operate the sensing devices independently and/or in conjunction with one or more emitting devices, which can be included in illumination component 42 and/or monitoring component 44. In an embodiment, monitoring component 44 includes a set of sensing devices, such as one or more imaging devices, which enables monitoring component 44 to acquire and/or derive/estimate data on various physical attributes of the organism 16, such as its size, color, weight, and/or the like. Additionally, monitoring component 44 can include sensing devices for directly sensing a composition of the organism 16, such as one or more chemical sensors, and/or the like. In an illustrative embodiment, monitoring component 44 includes a set of light sensing devices, which can detect an emission of ultraviolet and/or visible light from the organism 16 and store data corresponding to the detected emission(s) as fluorescence data for the organism 16.

Monitoring component 44 can determine a set of fluorescence characteristics of the organism 16 using the corresponding fluorescence data, which also can be stored as organism data 34. For example, the set of fluorescence characteristics can include one or more of: fluorescence intensity, a fluorescence polarization, a fluorescence time delay, a fluorescence spectrum, and/or the like. In an embodiment, monitoring component 44 can determine a set of visible fluorescence characteristics of the organism 16 using data acquired while the organism 16 is illuminated with visible light and determine a set of ultraviolet fluorescence characteristics of the organism 16 using data acquired while the organism 16 is illuminated with ultraviolet light. In a more specific embodiment, the visible light comprises chromatic light, such as blue or red light.

As discussed herein, monitoring component 44 also can include a set of sensing devices for acquiring environment data 36 on the organism environment 14. For example, monitoring component 44 can include one or more sensing devices for acquiring data corresponding to a temperature, a pressure (e.g., atmospheric pressure), a humidity level, a chemical composition of soil, air, water, and/or the like, etc.

Evaluation component 46 can dynamically determine a set of target properties of ultraviolet light for use in illuminating the organism 16 while managing illumination of the organism 16 during the managed period. In an embodiment, evaluation component 46 repeatedly determines the set of target properties during the managed period using the acquired organism data 34 and/or environment data 36. For example, evaluation component 46 can determine the set of target properties periodically, according to a fixed schedule. Additionally, evaluation component 46 can determine the set of target properties in response to an event, such as a request made by a user 12 (FIG. 1), an evaluated condition in acquired organism data 34 and/or environment data 36, and/or the like.

In an illustrative embodiment, evaluation component 46 determines the set of target properties based on the set of ultraviolet fluorescence characteristics of the organism 16 obtained by monitoring component 44 using a self-learning process. For example, evaluation component 46 can adjust one or more of the spectrum, intensity, polarization, spatial pattern, duration, constant/pulsing of the ultraviolet light according to the fluorescence intensity, polarization, time delay, spectrum, and/or the like, of the ultraviolet light using a self-learning process. In this case, evaluation component 46 can use feedback corresponding to the effect, if any, of an adjustment to one or more properties of the ultraviolet light, and evaluate its corresponding effect on the growth of the organism 16. Evaluation component 46 can evaluate the effectiveness of ultraviolet light having various sets of properties applied to multiple organisms 16 of the same or a similar species over a period of time. By combining the effectiveness of the results, evaluation component 46 can determine a set of target properties for the ultraviolet light, which is most effective for the organism 16.

In a more specific illustrative embodiment, evaluation component 46 determines the set of target properties based on a difference between the set of ultraviolet fluorescence characteristics and the set of visible ultraviolet fluorescence characteristics. For example, evaluation component 46 can determine a ratio between at least one of the set of ultraviolet fluorescence characteristics and the corresponding at least one of the set of visible fluorescence characteristics. Illustrative fluorescence characteristics comprise a position of peaks in the spectrums and line widths. In a more specific example, evaluation component 46 uses a set of visible fluorescence characteristics that are acquired while the organism 16 is illuminated with chromatic visible light, such as blue light or red light, which correspond to spectral lines required to grow plants.

Evaluation component 46 can determine the set of target properties of the ultraviolet light using the determined ratio (s). For example, evaluation component 46 can determine a target ultraviolet radiation intensity, a target spectral power distribution (e.g., generated by a multi-wavelength radiation source), and/or the like, using a self-learning process, which evolves by analyzing the impact of previous adjustments to property(ies) of the ultraviolet light on the ratio. Subsequently, evaluation component 36 can provide the set of target properties for use by the control component 40 in operating the illumination component 42. In particular, control component 40 can adjust the operation of one or more devices, such as the light emitting devices (e.g., DUV LEDs), to illuminate the organism 16 with ultraviolet light having a set of actual properties that corresponds to the set of target properties provided by evaluation component 46. In this manner, computer system 20A can implement a feedback and optimization process, which adjusts the illumination characteristics of the organism 16 based on feedback acquired from the organism 16 and/or the organism environment 14.

In an embodiment, evaluation component 46 can determine a preferred illumination cycle for illuminating the organism 16 with ultraviolet light based on the feedback and optimization process performed over a time period. For example, after the time period, evaluation component 46 can determine the properties of the ultraviolet light and aspects of illuminating the organism 16 with the ultraviolet light that produced a desired set of fluorescence characteristics for the organism 16. Evaluation component 46 can generate and store cycle data 48, such as a script, or the like, which can be subsequently used by a computer system to manage a set of conditions of an organism environment 14 during a managed time period, which includes managing ultraviolet illumination of another organism 16 of the same or a similar species as the organism 16. The cycle data 48 can include data defining the timing and at least one characteristic for each of a set of ultraviolet light illumination time periods. To this extent, the cycle data 48 can define a predetermined pattern of continuous and/or pulsed ultraviolet light illumination.

While evaluation component 46 can generate the cycle data 48 from the management of a single set of organisms 16 over a single managed time period, it is understood that evaluation component 46 can generate the cycle data 48 based on a combination of the results obtained from separately managing ultraviolet illumination of multiple organisms 16 of the same or a substantially similar subgenus or species. For example, evaluation component 46 can separately determine a preferred illumination cycle for each organism 16, and combine the results (e.g., by averaging the results) to generate the cycle data 48.

Regardless, when stored on a computer system, such as computer system 20 (FIG. 1), capable of processing the cycle data 48 to perform the preferred illumination cycle, the cycle data 48 creates a computing component configured to manage at least one condition of an organism environment 14 of another organism 16 of the same or a similar species as the organism 16 using the preferred illumination cycle.

Figure 3:
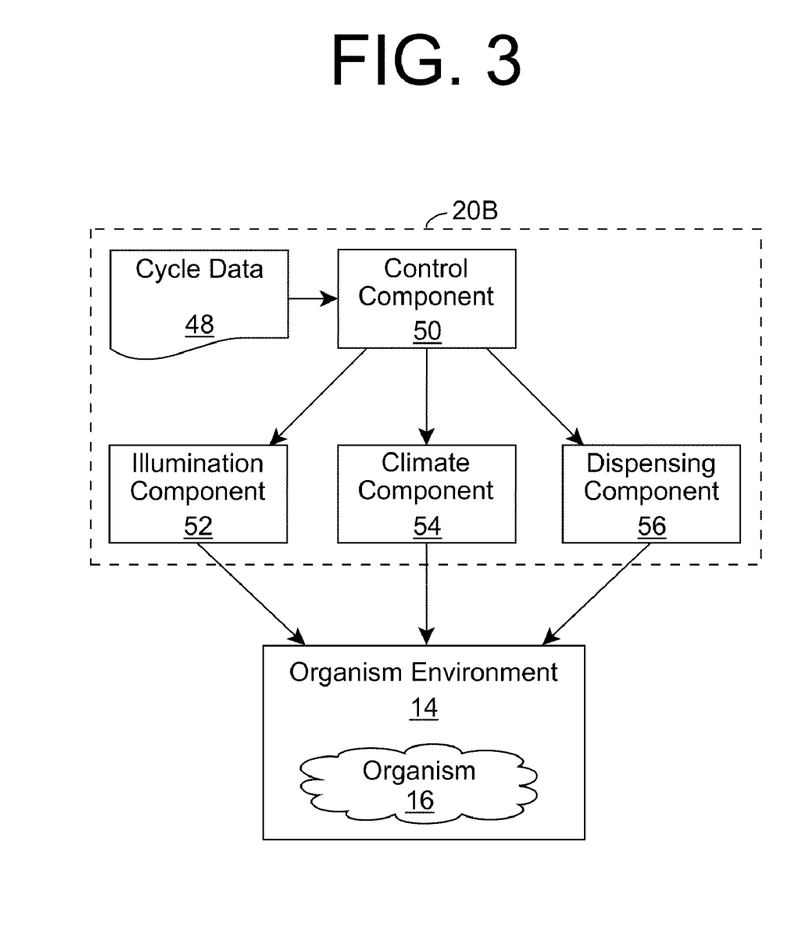
FIG. 3 shows a component view of still another illustrative computer system according to an embodiment.

To this extent, FIG. 3 shows a component view of still another illustrative computer system 20B according to an embodiment. Computer system 20B includes a control component 50, which is configured to manage a set of conditions of an organism environment 14 including an organism 16 during a managed time period by processing cycle data 48. To this extent, control component 50 can operate a set of light (e.g., visible, ultraviolet, and/or deep ultraviolet) emitting devices included in an illumination component 52 according to the cycle data 48. Illumination component 52 can be similarly configured as shown and described herein with respect to illumination component 42 (FIG. 2). Additionally, while not shown for clarity, control component 50 can manage and receive data from a monitoring component, which can be similarly configured as shown and described herein with respect to monitoring component 44 (FIG. 2).

Control component 50 also can manage one or more conditions of the organism environment 14 by operating a set of devices included in a climate component 54. Illustrative climate control devices can include, for example, a heating device, a cooling device, a humidifier, a dehumidifier, a compressor, a pump, and/or the like. Similarly, control component 50 also can manage the dispensation of one or more substances to preserve the organism 16, assist growth of the organism 16, and/or the like by operating a set of dispensing devices in a dispensing component 56. Illustrative dispensing devices can be configured to dispense, for example, water, fertilizer, plant growth regulators (e.g., herbicides, hormones, and/or the like), pesticides, nutrients, and/or the like.

Returning to FIG. 1, computer system 20 (e.g., an embodiment such as computer system 20A or 20B) can be utilized to manage one or more conditions of the organism environment 14 for the organism 16 as part of various applications for various types of organisms 16. For example, in an embodiment, computer system 20 manages one or more conditions of the organism environment 14 during a growth period for the organism 16. The growth period can comprise any portion of a time period during which the organism 16 is growing and/or reproducing. In this case, the organism 16 can comprise a plant, fungus, and/or animal, which is living and growing within the organism environment 14. Furthermore, the organism environment 14 can include a plurality of the same species of organism 16 and/or multiple species of organisms 16 that are living and growing therein.

In any event, computer system 20 can manage the ultraviolet illumination of the organism(s) 16 growing in the organism environment 14 during the growth period using a process described herein. Additionally, computer system 20 can manage one or more additional conditions of the organism environment 14, such as visible light illumination, temperature, and/or the like, using a process described herein.

In a more particular embodiment, the organism environment 14 is a greenhouse. In another more particular embodiment, the organism environment 14 is contained within a space-based structure (e.g., a space vehicle, space station, and/or the like), which is growing organism(s) 16 while in space. The organism environment 14 also can comprise a portion of an open area/environment. For example, the organism environment 14 can comprise a field, with a plurality of organisms 16 (e.g., plants) growing therein. In still another more particular embodiment, the organism environment 14 is a body of water, with organism(s) 16 growing underwater and/or on the surface of the water. In this case, computer system 20 can perform a method described herein in order to control plant growth, such as algae, control the growth of water borne animals, and/or the like. To this extent, computer system 20 can perform a method described herein in order to control fouling of water-borne vehicles, such as boats and large ships.

When the organism(s) 16 is (are) also being bred, computer system 20 can manage a process of breeding ultraviolet resistant plants. Such breeding can be used for increasing biomass for bio fuel applications, such as ethanol and/or biodiesel production.

In another application, computer system 20 manages one or more conditions of an organism environment 14 in which the organism 16 is maintained after being harvested. For example, in an embodiment, the organism environment 14 is a refrigerated area. The refrigerated area can be cooled by an electrical cooling system (which can be operated by computer system 20), packages of ice or other cooling materials, and/or the like. In any event, the organism environment 14 can be located within and/or implemented as part of a fixed storage facility, on a vehicle transporting the organism 16, and/or the like.

Figure 4:
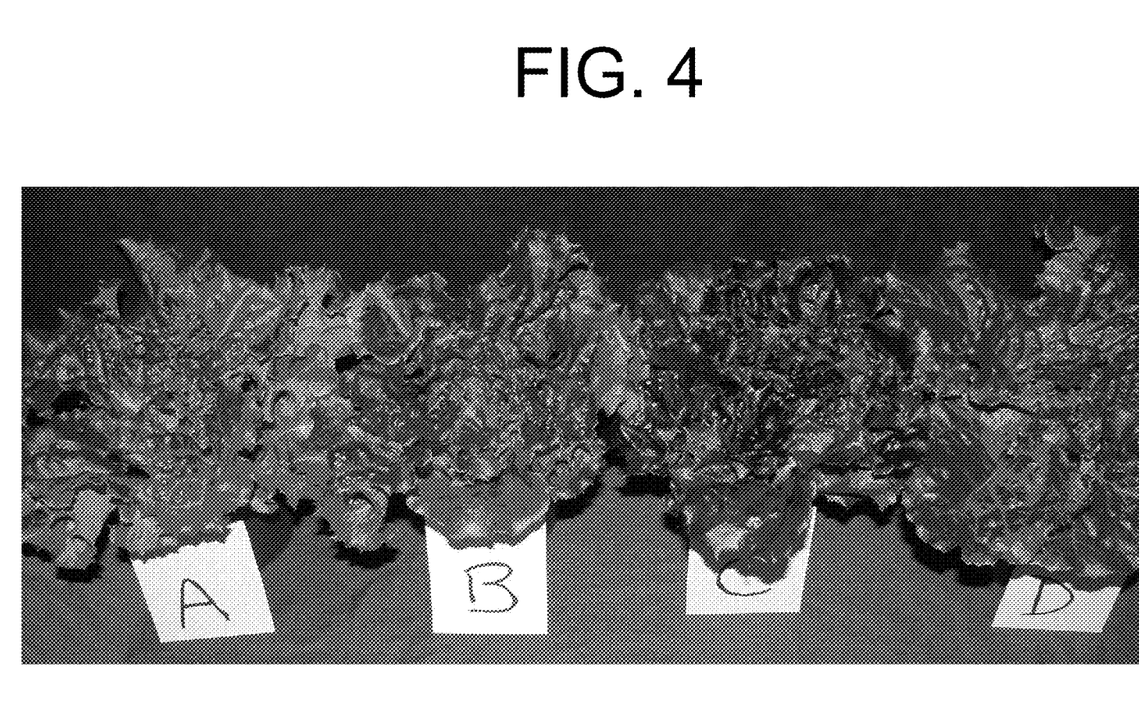
FIG. 4 shows red leaf lettuce after illumination with deep ultraviolet light after harvesting according to an embodiment.

Computer system 20 can manage illumination of the organism 16 with UV/DUV light after the organism 16 has been harvested and is stored in the organism environment 14. In an embodiment, the organism 16 is a plant, and computer system 20 performs a process of illuminating the organism 16 with UV/DUV light in order to, for example, increase one or more types of flavonoids in the organism 16. For example, FIG. 4 shows red leaf lettuce (cv. 'Galactic') after illumination with DUV light after harvesting according to an embodiment. The red leaf lettuce plants A, B, C, and D were grown in simulated winter greenhouse conditions (e.g., low photosynthetically-active and UV radiation) to reduce flavonoids. The plants A, B, C, D were stored for seven days at a temperature of approximately ten degrees Celsius and a relative humidity of approximately ninety percent. Plants A, D were not irradiated as controls. Plants B, C were irradiated for approximately twelve hours per day for each of the seven days. Plant B was irradiated with blue/UV-A radiation ($\lambda$>ca.

350 nm), while plant C was irradiated with blue/UV-A/UV-B radiation (λ>ca. 290 nm). As illustrated, plant C has substantially more red color, which results from an accumulation of anthocyanin cyandin-3-malonylglucoside, a type of flavonoid.

In the various applications and embodiments shown and described herein, computer system 20 and/or portions thereof (e.g., a set of sensors/emitters in I/O component 26) can be located within and/or remote from organism environment 14. For example, some or all of computer system 20 can be mounted on a vehicle, such as an airborne vehicle (e.g., aircraft, air balloon, drone, satellite, and/or the like), a land vehicle, and/or a waterborne vehicle (e.g., a ship), which can be utilized to manage large scale and/or multiple organism environments 14 using a process described herein. Such a vehicle can be manually operated and/or operated by computer system 20 to scan the organism environment(s) 14 in a predetermined sequence.

To this extent, a vehicle can comprise various sensors and/or emitters, which are controlled by a remotely or locally located computing device. The computing device can communicate with the sensors/emitters using any wireless communications solution, and utilizing any public and/or private communications network, such as the Internet. Additionally, a single computer system 20 can manage multiple organism environments 14. Furthermore, multiple computer systems 20 can share information via a public and/or private network. In this case, a process described herein can be improved through the substantially real time sharing of information among the various computer systems 20.

While shown and described herein as a method and system for managing at least one condition of an environment of an organism, it is understood that aspects of the invention further provide various alternative embodiments. For example, in one embodiment, the invention provides a computer program fixed in at least one computer-readable medium, which when executed, enables a computer system to manage at least one condition of an environment of an organism. To this extent, the computer-readable medium includes program code, such as management program 30 (FIG. 1), which implements some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; and/or the like.

In another embodiment, the invention provides a method of providing a copy of program code, such as management program 30 (FIG. 1), which implements some or all of a process described herein. In this case, a computer system can process a copy of program code that implements some or all of a process described herein to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of program code that implements some or all of a process described herein, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for managing at least one condition of an environment of an organism. In this case, a computer system, such as computer system 20 (FIG. 1), can be obtained (e.g., created, maintained, made available, etc.) and one or more components for performing a process described herein can be obtained (e.g., created, purchased, used, modified, etc.) and deployed to the computer system. To this extent, the deployment can comprise one or more of: (1) installing program code on a computing device; (2) adding one or more computing and/or I/O devices to the computer system; (3) incorporating and/or modifying the computer system to enable it to perform a process described herein; and/or the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A method comprising:
managing at least one condition of an environment of an organism for a managed time period using a computer system, the managing including repeatedly, during the managed time period:
determining a set of ultraviolet fluorescence characteristics of the organism using ultraviolet fluorescence data for the organism, wherein the ultraviolet fluorescence data is acquired while the organism is illuminated with ultraviolet light;
determining a set of target properties of the ultraviolet light based on the set of ultraviolet fluorescence characteristics; and
providing the set of target properties for use in illuminating the organism with ultraviolet light.

2. The method of claim 1, the managing further comprising:
generating ultraviolet light using a set of ultraviolet light emitting diodes (UV LEDs); and
illuminating the organism with ultraviolet light having a set of actual properties corresponding to the set of target properties using the generated ultraviolet light.

3. The method of claim 2, wherein the ultraviolet light comprises a peak wavelength in a range between approximately 200 nanometers and approximately 340 nanometers.

4. The method of claim 1, the managing further comprising periodically dispensing at least one of: water, fertilizer, or plant growth regulators for the organism during the managed time period.

5. The method of claim 1, the managing further comprising:
measuring a set of visible fluorescence characteristics of the organism while the organism is illuminated with chromatic visible light, the chromatic visible light being one of: blue light or red light; and
determining a ratio between at least one of the set of ultraviolet fluorescence characteristics and the at least one of the set of visible fluorescence characteristics, wherein the set of target properties are further determined using the ratio.

6. The method of claim 1, further comprising determining a preferred illumination cycle for the managing based on the managing, wherein the preferred illumination cycle defines timing and at least one characteristic for each of a plurality of ultraviolet light illumination time periods.

7. The method of claim 6, further comprising:
creating a computing component configured to manage at least one condition of an environment of another organism of the same species as the organism using the preferred illumination cycle; and
managing the at least one condition of the environment of the another organism using the computing component.

8. The method of claim 6, wherein the managing is separately performed for each of a plurality of organisms of the same species, wherein the preferred illumination cycle is determined based on a combination of the separately performed managing.

9. The method of claim 1, wherein the managed time period comprises a growth time period for the organism.

10. The method of claim 1, wherein the managed time period comprises a maintenance time period for the organism, wherein the maintenance time period occurs after the organism has been harvested.

11. A system comprising:
a computer system including at least one computing device configured to implement a method for managing at least one condition of an environment of an organism for a managed time period, the method including repeatedly, during the managed time period:
determining a set of ultraviolet fluorescence characteristics of the organism using ultraviolet fluorescence data for the organism, wherein the ultraviolet fluorescence data is acquired while the organism is illuminated with ultraviolet light;
determining a set of target properties of the ultraviolet light based on the set of ultraviolet fluorescence characteristics; and
providing the set of target properties for use in illuminating the organism with ultraviolet light.

12. The system of claim 11, the computer system further including a set of ultraviolet light emitting diodes (UV LEDs), wherein the managing further includes:
generating ultraviolet light using the set of UV LEDs; and
illuminating the organism with ultraviolet light having a set of actual properties corresponding to the set of target properties using the generated ultraviolet light.

13. The system of claim 11, the computer system further including a set of dispensing devices, wherein the managing further includes periodically dispensing at least one of: water, fertilizer, or plant growth regulators for the organism during the managed time period.

14. The system of claim 11, the computer system further including a set of climate control devices, wherein the managing further includes managing a set of conditions of a climate for the organism using the set of climate control devices.

15. The system of claim 11, the managing further including:
measuring a set of visible fluorescence characteristics of the organism while the organism is illuminated with chromatic visible light, the chromatic visible light being one of: blue light or red light; and
determining a ratio between at least one of the set of ultraviolet fluorescence characteristics and the at least one of the set of visible fluorescence characteristics, wherein the set of target properties are further determined using the ratio.

16. The system of claim 11, further comprising one of: a greenhouse or a body of water, wherein the organism is growing in the one of: the greenhouse or the body of water during the managed time period.

17. The system of claim 11, further comprising a refrigerated area, wherein the organism is maintained in the refrigerated area for the managed time period after being harvested.

18. A computer program comprising program code embodied in at least one computer-readable storage medium, which when executed, enables a computer system to implement a method of managing at least one condition of an environment of an organism for a managed time period, the method comprising:
determining a set of ultraviolet fluorescence characteristics of the organism using ultraviolet fluorescence data for the organism, wherein the ultraviolet fluorescence data is acquired while the organism is illuminated with ultraviolet light;
determining a set of target properties of the ultraviolet light based on the set of ultraviolet fluorescence characteristics; and
providing the set of target properties for use in illuminating the organism with ultraviolet light.

19. The computer program of claim 18, the method further comprising:
measuring a set of visible fluorescence characteristics of the organism while the organism is illuminated with chromatic visible light, the chromatic visible light being one of: blue light or red light; and
determining a ratio between at least one of the set of ultraviolet fluorescence characteristics and the at least one of the set of visible fluorescence characteristics, wherein the set of target properties are further determined using the ratio.

20. The computer program of claim 18, the method further comprising determining a preferred illumination cycle for the managing based on the managing, wherein the preferred illumination cycle defines timing and at least one characteristic for each of a plurality of ultraviolet light illumination time periods.

* * * * *